United States Patent
Luebke et al.

(10) Patent No.: US 10,563,137 B2
(45) Date of Patent: Feb. 18, 2020

(54) PROCESSES FOR REMOVING NITRILES FROM A FEED TO AN OLIGOMERIZATION ZONE

(71) Applicant: UOP LLC, Des Plaines, IL (US)

(72) Inventors: Charles P. Luebke, Mount Prospect, IL (US); Zhihao Fei, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/987,865

(22) Filed: May 23, 2018

(65) Prior Publication Data

US 2018/0265790 A1    Sep. 20, 2018

Related U.S. Application Data

(63) Continuation of application No. PCT/US2016/063035, filed on Nov. 21, 2016.
(Continued)

(51) Int. Cl.
| | | |
|---|---|---|
| *C10G 57/02* | (2006.01) | |
| *C07C 7/12* | (2006.01) | |
| *C10G 25/12* | (2006.01) | |
| *B01D 15/08* | (2006.01) | |
| *C10G 25/00* | (2006.01) | |
| *C10G 50/00* | (2006.01) | |
| *C10G 55/06* | (2006.01) | |
| *C10G 53/04* | (2006.01) | |
| *B01D 53/04* | (2006.01) | |
| *C07C 2/06* | (2006.01) | |
| *C07C 2/08* | (2006.01) | |

(Continued)

(52) U.S. Cl.
CPC ............. *C10G 57/02* (2013.01); *B01D 15/08* (2013.01); *B01D 53/0423* (2013.01); *C07C 2/06* (2013.01); *C07C 2/08* (2013.01); *C07C 2/12* (2013.01); *C07C 7/12* (2013.01); *C07C 7/13* (2013.01); *C10G 25/00* (2013.01); *C10G 25/003* (2013.01); *C10G 25/12* (2013.01); *C10G 50/00* (2013.01); *C10G 53/04* (2013.01); *C10G 55/06* (2013.01); *B01D 2253/108* (2013.01); *B01D 2256/24* (2013.01); *B01D 2257/40* (2013.01); *B01D 2259/40092* (2013.01); *C07C 2/02* (2013.01); *C07C 2/04* (2013.01); *C10G 2300/1088* (2013.01); *C10G 2300/202* (2013.01); *C10G 2400/02* (2013.01); *C10G 2400/04* (2013.01)

(58) Field of Classification Search
CPC .......................... C10G 2400/02; C10G 57/02; C10G 2400/04; C10G 25/003; C10G 53/04; C10G 55/06; C10G 50/00; C10G 25/00; C10G 25/12; C10G 2300/1088; C10G 2300/202; B01D 2257/40; B01D 2253/108; B01D 2256/24; B01D 53/0423; B01D 2259/40092; B01D 15/08; C07C 7/12; C07C 7/13; C07C 2/06; C07C 2/08; C07C 2/12; C07C 2/02; C07C 2/04
See application file for complete search history.

(56) References Cited

U.S. PATENT DOCUMENTS

2010/0113847 A1* 5/2010 Kowalik ................ C10G 50/00
                                                         585/20
2014/0330060 A1* 11/2014 Goris ........................ C07C 2/12
                                                         585/319

* cited by examiner

Primary Examiner — Ali Z Fadhel

(57) ABSTRACT

Processes for regenerating adsorbent in a nitrile removal zone. The regenerant comprises a stream of hot liquid that may comprise a portion of the oligomerized effluent or a portion of a hydrotreated effluent. A spent regenerant comprising the desorbed nitriles may be processed along with the oligomerized effluent with existing separation equipment.

14 Claims, 1 Drawing Sheet

Related U.S. Application Data

(60) Provisional application No. 62/267,452, filed on Dec. 15, 2015.

(51) Int. Cl.
*C07C 2/12* (2006.01)
*C07C 7/13* (2006.01)
*C07C 2/02* (2006.01)
*C07C 2/04* (2006.01)

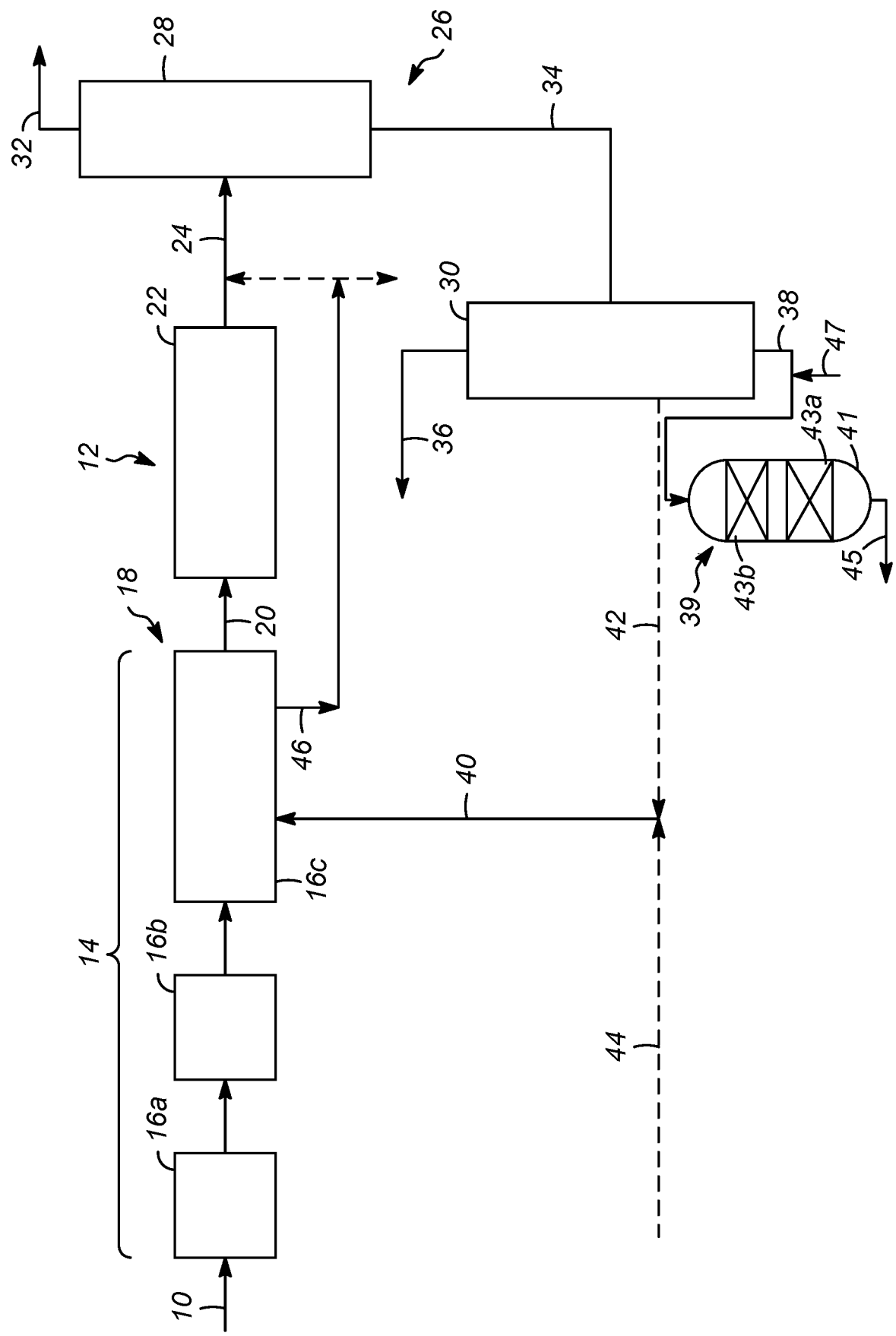

PROCESSES FOR REMOVING NITRILES FROM A FEED TO AN OLIGOMERIZATION ZONE

CROSS-REFERENCE TO RELATED APPLICATIONS

This application is a Continuation of copending International Application No. PCT/US2016/063035 filed Nov. 21, 2016, which application claims priority from U.S. Provisional Application No. 62/267,452 filed Dec. 15, 2015, the contents of which cited applications are hereby incorporated by reference in their entirety.

FIELD OF THE INVENTION

This invention relates generally to processes for removing contaminants from a feed stream to a reaction zone, and more particularly to processes for removing nitriles from a feed stream to an oligomerization zone.

BACKGROUND OF THE INVENTION

It is known to oligomerize low boiling range olefins into higher value products that have higher boiling points. For example, some oligomerization processes, process a feed stream comprising C4/C5 olefins and convert these components into diesel range products, as well as some gasoline blending components. In some refineries, the stream comprising C4/C5 olefins may originate from a fluidized catalytic cracking (FCC) unit.

The oligomerization of the C4/C5 olefins from an FCC utilize a catalyst that is sensitive to many contaminants contained in the feed stream. Accordingly, the feed stream to an oligomerization zone is typically treated in a pretreatment section to remove the various contaminants and inhibitors.

Typically, a pretreatment section contains various removal zones each configured to remove contaminants, such as sulfur compounds, di-olefins, oxygenates, nitriles or other contaminants or inhibitors that may be in the feed stream. Thus, a nitrile removal zone typically includes a nitrile removal unit (NRU) which is used to remove the trace levels of nitriles contained in the feed stream. The NRU is typically a swing bed adsorption system that requires an external regenerant stream to refresh the adsorbent bed by desorbing or removing the nitriles from the adsorbent.

In a conventional NRU, the regenerant stream is typically a C4 or C5 hydrocarbon stream that is free of these contaminants. This regenerant stream is vaporized and the spent adsorbent bed is heated with the vaporized stream and the contaminants are removed from the adsorbent. The unwanted contaminants, removed from the feed stream, are now transferred to the spent regenerant stream and the refreshed adsorbent bed is ready to be placed back on-line.

While these processes are presumably effective for their intended purposes, such regeneration processes rely upon a regenerant stream that may not be readily available in some or most refineries. Additionally, while an externally produced regenerant stream could be used, such streams can be costly.

Accordingly, it would be desirable to have one or more processes that efficiently and efficiently allow for the regeneration of a nitrile removal zone that do not require a C4/C5 vaporized regenerant stream. It would also be desirable if one or more of such processes utilized a regenerant stream that is readily available in most refineries.

SUMMARY OF THE INVENTION

One or more processes have been invented in which a hot liquid stream is used to regenerate absorbents in a nitrile removal zone. The regenerant stream may comprise portion of an effluent from a reaction zone, such as an oligomerization zone or a hydrotreating zone. The spent regenerant comprising the desorbed nitriles maybe combined with the reactor effluent and separated in a separation zone along with the effluent into a least one stream including the nitriles.

In a first aspect of the invention, the present invention may be characterized broadly as providing a process for removing nitriles from a feed stream for a reaction zone by: adsorbing nitriles from a feed stream in a nitrile removal zone having an adsorbent configured to selectively adsorb nitriles from the feed stream and provide a cleaned feed stream relatively free of nitriles; oligomerizing the cleaned feed stream in an oligomerization zone having a reactor containing a catalyst and configured to provide an oligomerized effluent; and, desorbing the nitriles from the nitrile removal zone with a regenerant stream comprising a hot liquid to provide a spent regenerant stream.

In at least one embodiment, the regenerant stream comprises a portion of the oligomerized effluent.

In at least one embodiment, the regenerant stream comprises a portion of a hydrotreated effluent.

In at least one embodiment, the feed stream comprises C3 to C7 hydrocarbons.

In at least one embodiment, the process includes separating the oligomerized effluent in a separation zone into a C4− stream, a diesel stream, and a gasoline stream. It is contemplated that the separation zone includes at least two columns and a first column from the at least two columns provides the C4− stream and a second column from the at least two columns provides the diesel stream and the gasoline stream. It is also contemplated that the second column further provides the regenerant stream. It is further contemplated that the regenerant stream comprises a sidecut stream from the second column, wherein the sidecut stream comprises C8 to C12 hydrocarbons.

In at least one embodiment, the process includes separating the spent regenerant stream into at least one stream including nitriles. It is contemplated that the spent regenerant stream is separated in a separation column with the oligomerized effluent.

In a second aspect of the present invention, the present invention may be broadly characterized as providing a process for removing nitriles from a feed stream for a reaction zone by: passing a feed stream comprising hydrocarbons and nitriles to a nitrile removal zone having an adsorbent configured to selectively adsorb nitriles from the feed stream and provide a cleaned feed stream relatively free of nitriles; passing the cleaned feed stream to an oligomerization zone having a reactor containing a catalyst and configured to provide an oligomerized effluent; passing the oligomerized effluent to a separation zone being configured to provide at least one C4− stream and at least one product stream; and, passing a regenerant stream comprising a hot liquid to the nitrile removal zone to desorb the nitriles and provide a spent regenerant stream, the spent regenerant stream including nitriles.

In at least one embodiment, the regenerant stream comprises a portion of a hydrotreated effluent.

In at least one embodiment, the regenerant stream comprises a portion of the oligomerized effluent. It is contemplated that the feed stream comprises a C3 to C7 hydrocarbon feed stream.

In at least one embodiment, the separation zone comprises at least two columns, wherein a first column provides the C4− stream, and wherein a second column provides the at least one product stream. It is contemplated that the second column provides the regenerant stream. It is further contemplated that the process includes passing the spent regenerant stream to the first column of the separation zone. It is even further contemplated that the spent regenerant stream and the oligomerized effluent are combined before being passed into the first separation column. It is contemplated that the regenerant stream comprises a C8 to C12 hydrocarbon stream. It is further contemplated that the feed stream comprises a portion of an effluent from a catalytic cracking zone.

Additional aspects, embodiments, and details of the invention, all of which may be combinable in any manner, are set forth in the following detailed description of the invention.

DETAILED DESCRIPTION OF THE DRAWING

One or more exemplary embodiments of the present invention will be described below in conjunction with the following drawing FIGURE, in which:

the FIGURE shows a process flow diagram according to one or more embodiments of the present invention.

DETAILED DESCRIPTION OF THE INVENTION

As mentioned above, one or more processes have been invented for regenerating adsorbent in a nitrile removal zone with a liquid regenerant stream. The nitrile removal zone is preferably disposed upstream of a reaction zone, and the regenerant may comprises a portion of the effluent from the reaction zone. In a preferred embodiment, the reaction zone comprises an oligomerization zone, and the regenerant comprises a portion of the oligomerized effluent. Alternatively, a stream of other liquid may be used as the regenerant, such as a portion of a hydrotreated effluent. Such hot liquid streams are readily available in most applications. Additionally, the use of such a stream allows for the spent regenerant in some instances to be separated along with the reactor effluent.

With these general principles in mind, one or more embodiments of the present invention will be described with the understanding that the following description is not intended to be limiting.

As shown in the FIGURE, a feed stream 10 for a reaction zone, for example, an oligomerization zone 12 is first passed to a pretreatment zone 14 that includes various units 16a, 16b, 16c for removing contaminants. Other reaction zones may also be used. Although not required to be, the feed stream 10 is preferably a portion of a cracked effluent, for example, a portion of an effluent from a fluid catalytic cracking (FCC) process. The FCC process typically produces a significant quantity of light olefins, for example, the total yield of C4 and C5 olefins from an FCC unit can be 20 wt % or more of the fresh feed. The C4 and C5 olefins are typically low value products. Accordingly, there is often a desire to convert these olefins into more desired product like diesel via oligomerization. For a detailed explanation of an exemplary FCC unit, reference is made to U.S. Pat. Pub. No. 2014/01435552, the entirety of which is incorporated herein by reference. In this application, hydrocarbon molecules may be abbreviated C1, C2, C3 . . . Cn where "n" represents the number of carbon atoms in the one or more hydrocarbon molecules. Furthermore, a superscript "+" or "−" may be used with an abbreviated one or more hydrocarbons notation, e.g., C4+ or C4−, which is inclusive of the abbreviated one or more hydrocarbons. As an example, the abbreviation "C4+" means one or more hydrocarbon molecules of three carbon atoms and/or more.

In addition to C4/C5 olefins, the feed stream 10 may also include light hydrocarbons, for example C3 hydrocarbons, as well as heavier hydrocarbons, such as C6 to C7 hydrocarbons. The C4 hydrocarbons includes butenes, i.e., C4 olefins, and butanes. Butenes include normal butenes and isobutene. The C5 hydrocarbons includes pentenes, i.e., C5 olefins, and pentanes. Pentenes include normal pentenes and isopentenes. Typically, the feed stream 10 will comprise about 20 to about 80 wt % olefins and suitably about 40 to about 75 wt % olefins. In an aspect, about 55 to about 75 wt % of the olefins may be butenes and about 25 to about 45 wt % of the olefins may be pentenes. Additionally, about 10 wt %, suitably 20 wt %, typically 25 wt % and most typically 30 wt % of the feed may be C5 olefins. In addition to the hydrocarbons, the feed stream 10 includes sulfur compounds, di-olefins, oxygenates, nitriles, each of which is removed or converted in the units 16a, 16b, 16c in the pretreatment zone 14.

One of the units 16a, 16b 16c in the pretreatment zone 14 comprises a nitrile removal zone 18. Other units 16a, 16b in the pretreatment zone 14 may include a sulfur removal zone, a selective hydrogenation zone, a water wash, or a bisulfite wash.

The nitrile removal zone 18 is configured to selectively adsorb nitriles, and possibly some oxygenates, from the feed stream 10 (which may or may not have been subjected to pretreatment in other units 16a, 16b in the pretreatment zone 14) and provide a cleaned feed stream 20 that is relatively free of nitriles. The nitrile removal zone 18 can use any suitable adsorbent for removing nitriles from the feed stream 10, which can be, for example, a zeolitic molecular sieve. Generally, the molecular sieve can include a zeolite X, Y, L, or a combination thereof. In addition, the adsorption conditions can be about 20 to about 80° C. (68 to 176° F.) and a pressure of about 100 to about 3,500 kPa (14.5 to 508 psi). Exemplary adsorbent beds and conditions are disclosed in, e.g., U.S. Pat. No. 5,271,835.

The nitrile removal zone 18 may include one or more, preferably two or more, adsorbent beds. Preferably, the nitrile removal zone 18 includes two or three vessels arranged in a lead-lag configuration (not shown), allowing for the feed stream 10 to be processed in one vessel while adsorbent in a second vessel is being regenerated (discussed below).

The cleaned feed stream 20, directly or after one or more additional pretreatment processes to remove other contaminants, is passed to the oligomerization zone 12 which includes at least one oligomerization reactor 22 containing a catalyst and being configured to provide an oligomerized effluent 24. Although not depicted as such the cleaned feed stream 20 may be preheated before entering the oligomerization reactor 22.

The oligomerization reactor 22 may be an upflow reactor to provide a uniform feed front through the catalyst bed, but other flow arrangements are contemplated. In an aspect, the oligomerization reactor 22 may contain an additional bed or beds of oligomerization catalyst. In the oligomerization zone 12, C4 olefins in the cleaned feed stream 20 oligomerize over the oligomerization catalyst to provide an oligomerate comprising C4 olefin dimers and trimers. Additionally, C5 olefins in the cleaned feed stream 20 oligomerize over the oligomerization catalyst to provide an oligomerate comprising C5 olefin dimers and trimers and co-oligomerize with C4 olefins to make C9 olefins. The oligomerization produces other oligomers with additional carbon numbers.

The operating conditions of the oligomerization zone 12 include exemplary operating pressures between about 2.1 MPa (300 psia) and about 10.5 MPa (1,520 psia), or between about 2.1 MPa (300 psia) and about 6.9 MPa (1,000 psia), or between about 2.8 MPa (400 psia) and about 4.1 MPa (600 psia). Lower pressures may be suitable if the reaction is kept in the liquid phase. The temperature of the oligomerization conditions in the oligomerization zone 12 expressed in terms of a maximum bed temperature is in a range between about 150 and about 300° C. (302 to 572° F.), or between 200 and about 250° C. (392 to 482° F.), or between about 225 and about 245° C. (437 to 473° F.). The space velocity may be between about 0.5 and about 5.0 $hr^{-1}$. Across a single bed of oligomerization catalyst, the exothermic reaction will cause the temperature to rise. Consequently, the oligomerization reactor 22 should be operated to allow the temperature at the outlet to be over about 25° C. (45° F.) greater than the temperature at the inlet.

The oligomerized effluent 24 from the oligomerization zone 12 may be passed to a separation zone 26 having one or more separation vessels to provide various product streams. For example, the separation zone 26 may comprise two separation columns 28, 30, each of which is a fractionation column. As used herein, the term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

A first separation column 28 may separate the oligomerized effluent 24 into an overhead stream 32 comprising C4 olefins and hydrocarbons and a liquid bottoms stream 34 comprising C5+ olefins and hydrocarbons. The liquid bottoms stream 34 may be passed to the second fractionation column 30 to be separated into different streams, for example a gasoline stream 36, typically comprising C5 to C9 hydrocarbons, and a diesel range stream 38, typically comprising C10 to C16 hydrocarbons. The gasoline stream 36 and the diesel range stream 38 may be processed further, for example, the diesel range stream 38 being passed to a hydrotreating zone 39 to remove heteroatoms to provide a diesel fuel stream. As used herein, the term "diesel" can include hydrocarbons having a boiling point temperature in the range of 150 to 400° C. (302 to 752° F.) and preferably 200 to 400° C. (392 to 752° F.). As used herein, the term "gasoline" can include hydrocarbons having a boiling point temperature in the range of 25 to 200° C. (77 to 392° F.) and at atmospheric pressure.

The hydrotreating zone 39 includes a hydrotreating reactor 41. The hydrotreating zone 39 shown in the FIGURE has one hydrotreating reactor 41; however, more than one hydrotreating reactor 41 may be utilized. Each hydrotreating reactor 41 may have one or more beds 43a, 43b of a suitable hydroprocessing catalyst. A hydroprocessed diesel stream 45 exits the hydrotreating zone 39.

The hydrotreating reactor 41 in the hydrotreating zone 39 may be operated in a continuous liquid phase, in a continuous gas phase, or with a mixture of gas and liquid.

During the hydrotreating reactions occurring in the hydrotreating reactor 41, hydrogen is necessarily consumed. Accordingly, the diesel range stream 38 may be mixed with a hydrogen stream 47 prior to entering the hydrotreating reactor 41. Additionally, hydrogen may be provided to the hydrotreating reactor 41 at one or more hydrogen inlet points (not shown) located downstream of the feed inlet for the diesel range stream 38. The flow rate of hydrogen added at these downstream locations is controlled to ensure that the reactor operates in a continuous liquid phase.

In some aspects, the diesel range stream 38 does not contain recycled product comprising a portion of the hydroprocessed diesel stream 45 or other hydrocarbon diluent. In other aspects, a recycle stream or diluent (both not shown) may be incorporated into the fresh diesel range stream 38 prior to hydrotreating to feed additional volume to the hydrotreating reactor 41 to provide added hydrogen-carrying capacity to the diesel range stream 38 or to provide additional mass to reduce the temperature rise in catalyst beds 43a, 43b. In such aspects, any recycled product or diluent typically is introduced into the diesel range stream 38 before the hydrogen in line 47 is mixed with the diesel range stream 38. Typically, such recycled product may be previously stripped of a vaporous hydrogen sulfide, nitrogen or nitrogen containing compositions, and any other vapor phase materials.

In the hydrotreating zone 39, hydrogen gas is contacted with the hydrocarbons in the diesel range stream 38 in the presence of suitable catalysts which are primarily active for the removal of heteroatoms, such as sulfur and nitrogen from the hydrocarbon feedstock. Additionally, unsaturated hydrocarbons are saturated.

Suitable hydrotreating catalysts for use in the present invention are any known conventional hydrotreating catalysts and include those which are comprised of at least one Group VIII metal, preferably iron, cobalt and nickel, more preferably cobalt and/or nickel and at least one Group VI metal, preferably molybdenum and tungsten, on a high surface area support material, preferably alumina. Other suitable hydrotreating catalysts include zeolitic catalysts, as well as noble metal catalysts where the noble metal is selected from palladium and platinum. It is within the scope of the present invention that more than one type of hydrotreating catalyst be used. The Group VIII metal is typically present in an amount ranging from about 2 to about 20 wt %, preferably from about 4 to about 12 wt %. The Group VI metal will typically be present in an amount ranging from about 1 to about 25 wt %, preferably from about 2 to about 25 wt %.

Suitable hydrotreating reaction conditions include a temperature from about 204 to about 482° C. (400 to 900° F.), preferably no more than 388° C. (730° F.), a pressure from about 3.5 to about 17.3 MPa (500 to 2500 psig), preferably no more than 10,342 kPa (1500 psig), a liquid hourly space velocity of the fresh hydrocarbonaceous feedstock (i.e., the diesel range stream 38) from about 0.1 $hr^{-1}$ to about 10 $hr^{-1}$ with a hydrotreating catalyst or a combination of hydrotreating catalysts. In an aspect, the hydrotreated diesel stream 45 (i.e., the hydrotreated effluent) has a lower sulfur concentration and an improved cetane number than that of the diesel range stream 38. The further processing of the hydrotreated diesel stream 45 is not important to the practicing of the present invention.

Returning to the nitrile removal zone 18, eventually the adsorbent will be become spent, requiring regeneration to desorb the nitriles and regenerate the adsorbent. Accordingly, a regenerant stream 40 comprising a hot liquid is utilized to desorb the nitriles. By "hot" it is meant that the regenerant stream 40 has a temperature between about 175 to 275° C. (347 to 527° F.), or between about 200 to 250° C. (392 to 482° F.), or about 230° C. (446° F.). In the prior art designs, a regenerant stream comprised vapor, typically with C4/C5 hydrocarbons. Again, such a vapor stream may not be readily available; however, various hot liquid streams having low levels of nitriles are typically readily available in most refineries.

Accordingly, in one embodiment, the regenerant stream 40 may comprise a portion of the oligomerized effluent 24 without further conversion or treating. For example, the regenerant stream 40 may comprise a stream from the separation zone 26. In at least one embodiment, the regenerant stream 40 comprises a sidecut stream 42 from the second fractionation column 30 in the separation zone 26. Preferably, the sidecut stream 42 comprises a range of C8 to C12 hydrocarbons. However, in some instances, the use of the oligomerized effluent 24, or a portion thereof, may not be desirable, for example depending on the amount of dienes in the sidecut stream 42.

Accordingly, it is also contemplated that in one or more embodiments, at least a portion of a hydrotreated effluent is used as the regenerant stream 40. For example, a diesel fuel stream 44 from a hydrotreating unit (not shown) be used as the regenerant stream 40. It is contemplated that the diesel fuel stream 44 comprises at least a portion of the diesel range stream 38 that has been hydrotreated, such as the hydrotreated diesel stream 45 from the hydrotreating zone 39. Other readily available hot liquid streams may be used in accordance with the present invention as the regenerant stream 40.

A spent regenerant stream 46, including the desorbed nitriles, may be removed from the nitrile removal zone 18. In at least one embodiment, the spent regenerant 46 is combined and passed to the separation zone 26 along with the oligomerized effluent 24. Although it is depicted that the spent regenerant 46 and the oligomerized effluent 24 are combined, it is also contemplated that each is passed into the separation zone 26 independently.

In the depicted exemplary embodiment, the nitriles will separate out with the overhead stream 32 of the first fractionation column 28. The hydrocarbons in the regenerant, will mostly comprise components in the liquid bottoms stream 34 that can be processed and separated as described above.

Alternatively, in some embodiments, the nitriles in the spent regenerant stream 46 may be less than 100 ppm. In at least one embodiment, it is contemplated that the spent regenerant 46 may be passed to a fuel blending pool (not shown). Furthermore, it is also contemplated that the spent regenerant 46 is passed to the hydrotreating zone 39.

In the present invention, various processes for regeneration for a nitrile removal zone are provided which utilize a readily available hot liquid regenerant. In addition to being more readily available that prior art streams, the use of the hot liquid may lower operating utilities since it will not need to be vaporized. In embodiments in which a portion of oligomerized effluent is used, the process will provide a readily available stream of hot liquid that is relatively free of contaminants. Additionally, in various embodiments, the use of the hot liquid allows for the use of existing equipment to separate nitriles from the liquid hydrocarbons of the regenerant.

Specific Embodiments

While the following is described in conjunction with specific embodiments, it will be understood that this description is intended to illustrate and not limit the scope of the preceding description and the appended claims.

A first embodiment of the invention is a process for removing nitriles from a feed stream for a reaction zone, the process comprising adsorbing nitriles from a feed stream in a nitrile removal zone having an adsorbent configured to selectively adsorb nitriles from the feed stream and provide a cleaned feed stream relatively free of nitriles; oligomerizing the cleaned feed stream in an oligomerization zone having a reactor containing a catalyst and configured to provide an oligomerized effluent; and, desorbing the nitriles from the nitrile removal zone with a regenerant stream comprising a hot liquid to provide a spent regenerant stream. An embodiment of the invention is one, any or all of prior embodiments in this paragraph up through the first embodiment in this paragraph wherein the regenerant stream comprises a portion of the oligomerized effluent. An embodiment of the invention is one, any or all of prior embodiments in this paragraph up through the first embodiment in this paragraph wherein the regenerant stream comprises a portion of a hydrotreated effluent. An embodiment of the invention is one, any or all of prior embodiments in this paragraph up through the first embodiment in this paragraph wherein the feed stream comprises C3 to C7 hydrocarbons. An embodiment of the invention is one, any or all of prior embodiments in this paragraph up through the first embodiment in this paragraph further comprising separating the oligomerized effluent in a separation zone into a C4− stream, a diesel stream, and a gasoline stream. An embodiment of the invention is one, any or all of prior embodiments in this paragraph up through the first embodiment in this paragraph wherein the separation zone includes at least two columns and wherein a first column of the at least two columns provides the C4− stream and wherein a second column of the at least two columns provides the diesel stream and the gasoline stream. An embodiment of the invention is one, any or all of prior embodiments in this paragraph up through the first embodiment in this paragraph wherein the second column further provides the regenerant stream. An embodiment of the invention is one, any or all of prior embodiments in this paragraph up through the first embodiment in this paragraph wherein the regenerant stream comprises a sidecut stream from the second column, wherein the sidecut stream comprises C8 to C12 hydrocarbons. An embodiment of the invention is one, any or all of prior embodiments in this paragraph up through the first embodiment in this paragraph further comprising separating the spent regenerant stream into at least one stream with nitriles. An embodiment of the invention is one, any or all of prior embodiments in this paragraph up through the first embodiment in this paragraph wherein the spent regenerant stream is separated in a separation column with the oligomerized effluent.

A second embodiment of the invention is a process for removing nitriles from a feed stream for a reaction zone, the process comprising passing a feed stream comprising hydrocarbons and nitriles to a nitrile removal zone having an adsorbent configured to selectively adsorb nitriles from the feed stream and provide a cleaned feed stream relatively free of nitriles; passing the cleaned feed stream to an oligomerization zone having a reactor containing a catalyst and configured to provide an oligomerized effluent; passing the oligomerized effluent to a separation zone being configured to provide at least one C4− stream and at least one product stream; and, passing a regenerant stream comprising a hot liquid to the nitrile removal zone to desorb the nitriles and provide a spent regenerant stream, the spent regenerant stream including nitriles. An embodiment of the invention is one, any or all of prior embodiments in this paragraph up through the second embodiment in this paragraph wherein the regenerant stream comprises a portion of a hydrotreated effluent. An embodiment of the invention is one, any or all of prior embodiments in this paragraph up through the second embodiment in this paragraph wherein the regenerant stream comprises a portion of the oligomerized effluent. An embodiment of the invention is one, any or all of prior embodiments in this paragraph up through the second embodiment in this paragraph wherein the feed stream comprises a C3 to C7 hydrocarbon feed stream. An embodiment of the invention is one, any or all of prior embodiments in this paragraph up through the second embodiment in this paragraph wherein the separation zone comprises at least two columns, wherein a first column provides the C4− stream, and wherein a second column provides the at least one product stream. An embodiment of the invention is one, any or all of prior embodiments in this paragraph up through the second embodiment in this paragraph, wherein the second column provides the regenerant stream. An embodiment of the invention is one, any or all of prior embodiments in this paragraph up through the second embodiment in this paragraph further comprising passing the spent regenerant stream to the first column of the separation zone. An embodiment of the invention is one, any or all of prior embodiments in this paragraph up through the second embodiment in this paragraph wherein the spent regenerant stream and the oligomerized effluent are combined before being passed into the first separation column. An embodiment of the invention is one, any or all of prior embodiments in this paragraph up through the second embodiment in this paragraph wherein the regenerant stream comprises a C8 to C12 hydrocarbon stream. An embodiment of the invention is one, any or all of prior embodiments in this paragraph up through the second embodiment in this paragraph wherein the feed stream comprises a portion of an effluent from a catalytic cracking zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

It should be appreciated and understood by those of ordinary skill in the art that various other components such as valves, pumps, filters, coolers, etc. were not shown in the drawing as it is believed that the specifics of same are well within the knowledge of those of ordinary skill in the art and a description of same is not necessary for practicing or understanding the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for removing nitriles from an oligomerization zone feed stream with an adsorbent and for desorbing nitriles from the adsorbent, the process comprising:
    adsorbing nitriles from the feed stream in a nitrile removal zone having at least two vessel, each vessel comprising an adsorbent configured to selectively adsorb nitriles from the feed stream and provide a cleaned feed stream with a reduced amount of nitriles compared to the feed stream;
    oligomerizing the cleaned feed stream in the oligomerization zone in the presence of a catalyst to provide an oligomerized effluent;
    separating the oligomerized effluent in a separation zone into a plurality of product streams having different hydrocarbon compositions, including a stream comprising C8 to C12 hydrocarbons; and,
    desorbing the nitriles from the nitrile removal zone with a hot liquid regenerant stream comprising the stream comprising C8 to C12 hydrocarbons,
    wherein nitriles are adsorbed from the feed stream in first vessel of the nitrile removal zone while nitriles are being desorbed with the hot liquid regenerant stream in the second vessel of the nitrile removal zone, and,
    wherein the regenerate stream is hydrotreated before the desorbing the nitriles from the nitrile removal zone.

2. The process of claim 1 wherein the feed stream comprises C3 to C7 hydrocarbons.

3. The process of claim 1 wherein the plurality of product streams comprise a C4− stream, a diesel stream, and a gasoline stream.

4. The process of claim 3 wherein the separation zone includes at least two columns and wherein a first column from the at least two columns provides the C4− stream and wherein a second column from the at least two columns provides the diesel stream and the gasoline stream.

5. The process of claim 4 wherein the spent regenerate stream and the oligomerized effluent are combined before being passed into the first column.

6. The process of claim 4 wherein the second column further provides the regenerate stream.

7. The process of claim 6 wherein the regenerate stream is obtained from a sidecut stream from the second column.

8. The process of claim 1 further comprising:
    separating the spent regenerate stream into a least one stream with nitriles.

9. The process of claim 8 wherein the spent regenerate stream is separated in the separation zone with the oligomerized effluent.

10. A process for removing nitriles from an oligomerization zone feed stream with an adsorbent and for desorbing nitriles from the adsorbent the process comprising:

passing the feed stream comprising hydrocarbons and nitriles to a nitrile removal zone comprising at least two vessels, each vessel having an adsorbent configured to selectively adsorb nitriles from the feed stream and provide a cleaned feed stream with a reduced amount of nitriles compared to the feed stream;

passing the cleaned feed stream to the oligomerization zone and oligomerizing the cleaned feed stream in the presence of a catalyst to provide an oligomerized effluent;

passing the oligomerized effluent to a separation zone being configured to provide a plurality of product streams having different hydrocarbon compositions, the product streams including at least one C4− stream and at least one C8 to C12 stream;

hydrotreating, in a hydrotreating zone, the C8 to C12 stream in the presence of a catalyst configured to selective remove heteroatoms and provide a hydrotreated effluent; and, passing a hot liquid regenerate stream comprising a portion of the hydrotreated effluent to the nitrile removal zone to desorb the nitriles and provide a spent regenerate stream, wherein nitriles are adsorbed from the feed stream in first vessel of the nitrile removal zone while nitriles are being desorbed with the hot liquid regenerant stream in the second vessel of the nitrile removal zone.

11. The process of claim 10 wherein the feed stream comprises a C3 to C7 hydrocarbon feed stream.

12. The process of claim 10 wherein the separation zone comprises at least two columns, wherein a first column provides the C4-stream, and wherein a second column provides the C8 to C12 stream.

13. The process of claim 10 further comprising:
passing the spent regenerate stream to the first column of the separation zone.

14. The process of claim 10 wherein the feed stream comprises a portion of an effluent from a catalytic cracking zone.

\* \* \* \* \*